US00PP23887P2

(12) United States Plant Patent
Sorensen

(10) Patent No.: US PP23,887 P2
(45) Date of Patent: Sep. 10, 2013

(54) ***CLEMATIS* PLANT NAMED 'YAKU010A'**

(50) Latin Name: ***Clematis* hybrid**
Varietal Denomination: YAKU010A

(76) Inventor: Peer Sorensen, Waitara (NZ)

( * ) Notice: Subject to any disclaimer, the term of this patent is extended or adjusted under 35 U.S.C. 154(b) by 177 days.

(21) Appl. No.: 13/134,657

(22) Filed: Jun. 13, 2011

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Cassandra Bright

(57) ABSTRACT

A new and distinct *Clematis* hybrid named 'YAKU010A' is disclosed, characterized by a distinctive feathery double flowers with a transparent quality to the tepals. Double flowers are produced with the first flush of flower, on previous year's wood. The new cultivar is a *Clematis* typically suited for ornamental container and landscape use.

2 Drawing Sheets

Latin name of the genus and species: *Clematis* hybrid.
Variety denomination: 'YAKU010A'.

BACKGROUND OF THE INVENTION

The new cultivar is the result of a chance discovery in a private garden in British Columbia, Canada. The inventor is Peer Sorensen, a citizen of New Zealand. The new variety was discovered as a single whole plant, mutation of the parent variety, an unpatented, unnamed variety of *Clematis* hybrid. The discovery was made in September of 2010.

After selecting and isolating the new cultivar, asexual reproduction of the new cultivar 'YAKU010A' was first performed in a commercial nursery in Apopka, Fla. by vegetative cuttings in the Fall of 2010. 'YAKU010A' has since produced multiple generations and has shown that the unique features of this cultivar are stable and reproduced true to type.

SUMMARY OF THE INVENTION

The cultivar 'YAKU010A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'YAKU010A'. These characteristics in combination distinguish 'YAKU010A' as a new and distinct *Clematis* cultivar:

1. Double "feathery" flowers
2. Pink tepals with a raspberry pink bar in center.
3. Large number of tepals per flower.
4. Transparent quality to tepals.
5. Double flowers produced on first flush of flowers, on previous year's wood.

PARENTAL COMPARISON

Plants of the new cultivar 'YAKU010A' are similar to the parent variety in most horticultural characteristics. However, 'YAKU010A' differs in having a more delicate appearance to the flower, and a more transparent appearance to the tepals than the parent variety.

COMMERCIAL COMPARISON

Plants of the new cultivar 'YAKU010A' are similar to the commercial variety *Clematis* hybrid 'Andromeda' unpatented, in most horticultural characteristics. 'Andromeda' may also produce semi-double flowers in the first flush on previous year's wood. 'YAKU010A' differs from 'Andromeda' flower color, as 'Andromeda' has lighter colored flowers. Additionally, plants of 'YAKU010A' continue to produce double flowers, whereas 'Andromeda' will often produce single flowers later in the Summer.

BRIEF DESCRIPTION OF THE PHOTOGRAPHS

Figure 1:
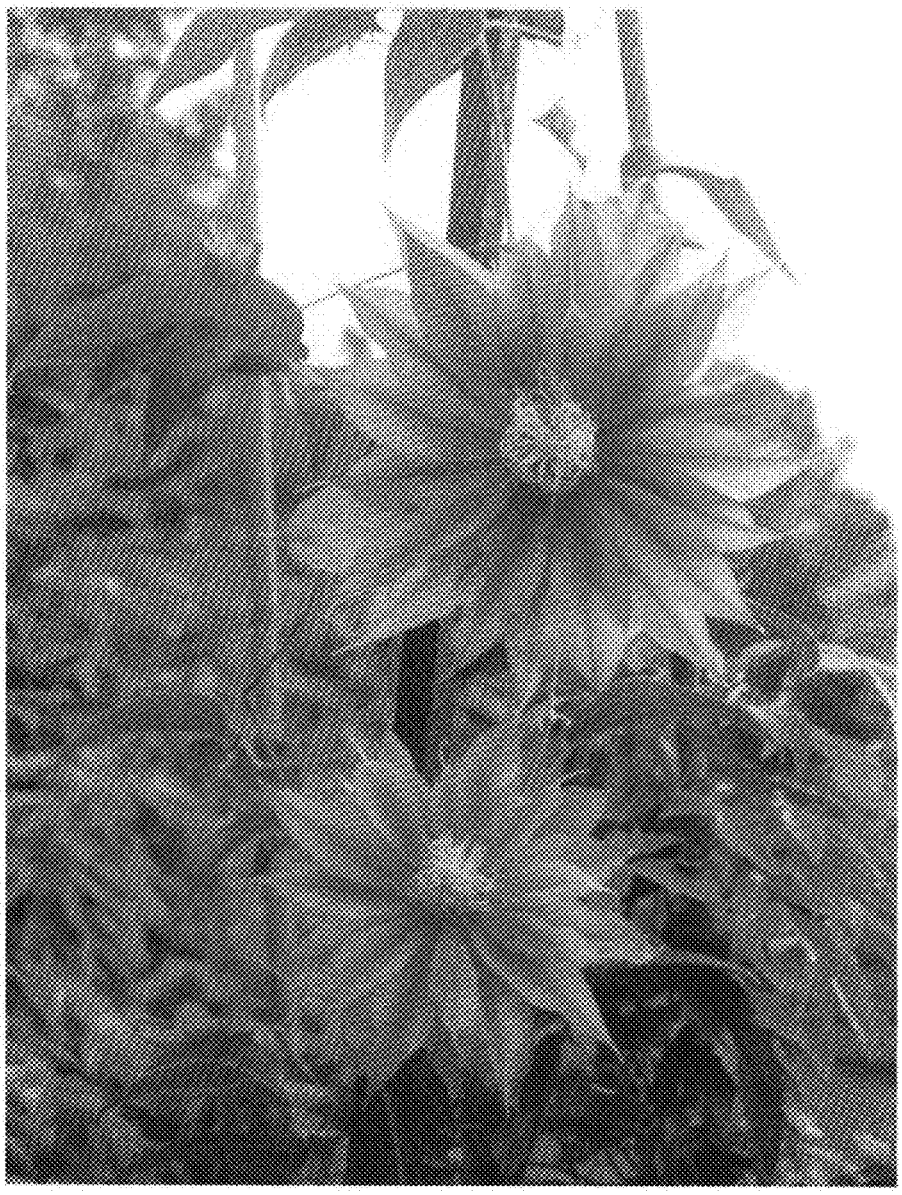

The accompanying photograph in FIG. 1 illustrates in full color a typical plant of 'YAKU010A' grown outdoors in British Columbia, Canada. This plant is approximately 8 months old, grown in the ground.

Figure 2:
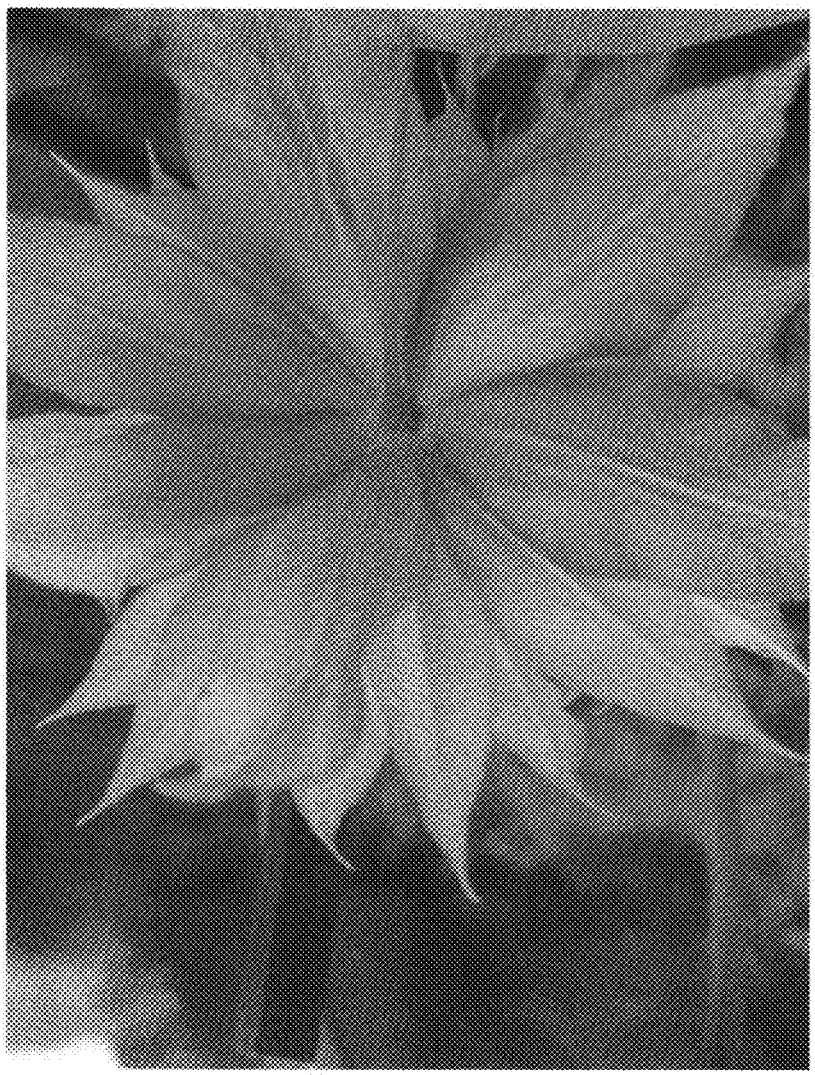

FIG. 2 illustrates in full color the back side of the flower, and the typical transparent quality of the tepals. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'YAKU010A' plants grown outdoors in British Columbia, Canada. Measurements were taken in May. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis* hybrid 'YAKU010A'.
Age of the plant described: Approximately 8 months
Container size of the plant described: Growing in the ground.

PROPAGATION

Typical method: Vegetative cuttings.
Time to initiate rooting: Approximately 20 days at 21° C. or higher.
Time to produce a rooted plantlet: Approximately 20 days at 20° C. or higher.
Root description: Fine, fibrous.

PLANT

Growth habit: Climbing vine.
Height: Approximately 250 cm, measured from the soil line of the pot after approximately 9 months.
Plant spread: Approximately 150 cm.
Growth rate: Rapid. During active growing season in Spring, approximately 150 cm per month.
Branching characteristics: One main stem.
Length of main stem: Approximately 200 cm.
Diameter of main stem: Approximately 0.2 to 0.5 cm.
Main stem color: Near RHS Brown 200B.
Main stem texture: Glabrous.
Internode length: Varies from 8 to 15 cm.
Strength: Strong, flexible, semi-woody.

FOLIAGE

Leaf:
- *Arrangement*.—Opposite, simple on lower stem, to ternate on upper stem.
- *Average length*.—Approximately 6 to 10 cm.
- *Average width*.—approximately 4.0 7.5 cm.
- *Shape of blade*.—Oblong to cordate.
- *Apex*.—Cuspidate.
- *Base*.—Cordate.
- *Attachment*.—Stalked.
- *Margin*.—Entire.
- *Texture of both surfaces*.—Slightly bullate.
- *Color*.—Young foliage upper side: Near RHS Green 137A. Young foliage under side: Near RHS Green 137C. Mature foliage upper side: Near RHS Green 137A. Mature foliage under side: Near RHS Green 137C.
- *Venation*.—Type: Pinnate. Venation color upper side: Near RHS Yellow-Green 145C. Venation color under side: Near RHS Yellow-Green 145B.

Petiole:
- *Length*.—Approximately 2.0 to 5.0 cm.
- *Diameter*.—Approximately 0.2 cm.
- *Texture*.—Smooth.
- *Color*.—Near RHS Greyed-Green 191A.

FLOWER

Bloom period:
- *Natural season*.—Continuously May through September.

Inflorescence type and habit: Single occurring, axillary; double flowers facing outward.
Rate of flower opening: Approximately 7 days from bud to fully opened flower.
Flower longevity on plant: Approximately 8 to 15 days, after fully opened. Self-cleaning.
Inflorescence size:
- *Diameter*.—Approximately 15 to 17 cm.
- *Depth*.—Approximately 5 cm.

Corolla:
- *Tepal arrangement*.—Slightly overlapping double or triple whorl.
- *Quantity*.—Approximately 20 to 50 per flower.
- *Size*.—Length: Approximately 4.5 to 10 cm. Width: Approximately 1.5 to 3.0 cm.
- *Margin*.—Slightly curved.
- *Apex*.—Acuminate.
- *Base*.—Obtuse. Texture: Smooth.
- *Shape*.—Ovate.

Color:
- *Tepals*.—When opening: Upper surface: Near RHS Purple 76D with bar near Red-Purple 71A. Lower surface: Near RHS Purple 76D with bar near Yellow-Green 144C. Fully opened: Upper surface: Near RHS Red-Purple 70C center bar near Red-Purple 71B, edges lighter. Lower surface: Near RHS Red-Purple 70D with center bar near Yellow-Green 144C. Edges flushed near 71D. Ageing: Upper Surface: Near RHS Red-Purple 70D, bar near 70C. Lower Surface: Near RHS Red-Purple 70D with center bar near Yellow-Green 144D.

Bud:
- *Shape*.—Conical.
- *Length*.—Approximately 2.5 cm.
- *Diameter*.—Approximately 1.5 to 1.8 cm.
- *Color*.—Near RHS Red-Purple 71B.

Pedicels:
- *Length*.—Approximately 10 to 25 cm.
- *Width*.—Approximately 1.5 to 3.0 cm.
- *Angle*.—Average 45° to 80°.
- *Strength*.—Flexible.
- *Color*.—Near RHS Yellow-Green 144A.

Fragrance: None.

REPRODUCTIVE ORGANS

Stamens:
- *Number*.—More than 40 per flower.
- *Anther length*.—Approximately 1.5 cm.
- *Anther color*.—Near RHS Yellow 16A.
- *Anther shape*.—Oblong.
- *Pollen quantity*.—Moderate.
- *Pollen color*.—Greyed-Yellow 162D.

Pistil:
- *Length*.—Approximately 2 cm.
- *Style length*.—Approximately 0.6 to 0.8 cm.
- *Stigma*.—Shape: Fine irregular hairs. Color: Near RHS Yellow-Green 154C, but lighter.

OTHER CHARACTERISTICS

Seeds and fruits: Not observed to date.
Disease/pest resistance: Neither resistance nor susceptibility to normal diseases and pests of *Clematis* has been observed.
Temperature tolerance: Tolerates temperatures from approximately −20° C. to 45° C.

What is claimed is:

1. A new and distinct cultivar of *Clematis* hybrid plant named 'YAKU010A' as herein illustrated and described.

* * * * *